United States Patent [19]
Ogden

[11] Patent Number: 6,070,103
[45] Date of Patent: May 30, 2000

[54] APPARATUS FOR MAKING DIRECT ELECTRICAL CONNECTION WITH AN IMPLANTABLE MEDICAL DEVICE

[75] Inventor: Robert R. Ogden, Lake Jackson, Tex.

[73] Assignee: Intermedics Inc., Angleton, Tex.

[21] Appl. No.: 08/743,316

[22] Filed: Nov. 5, 1996

[51] Int. Cl.$^7$ .................................................. A61N 1/00
[52] U.S. Cl. ............................... 607/60; 607/32; 607/33
[58] Field of Search .................................. 607/2, 30, 32, 607/33, 37, 60, 59

[56] References Cited

U.S. PATENT DOCUMENTS

| | | | |
|---|---|---|---|
| 4,146,029 | 3/1979 | Ellinwood, Jr. | 607/9 X |
| 4,712,557 | 12/1987 | Harris | 128/419 |
| 4,804,054 | 2/1989 | Howson et al. | 128/898 |
| 4,915,113 | 4/1990 | Holman | 128/691 |
| 4,941,472 | 7/1990 | Moden et al. | 128/419 |
| 5,131,854 | 7/1992 | Jose et al. | 439/86 |
| 5,205,286 | 4/1993 | Soukup et al. | 128/630 |
| 5,411,537 | 5/1995 | Munshi et al. | 607/33 |

FOREIGN PATENT DOCUMENTS

2568477  2/1986  France ..................................... 607/33

*Primary Examiner*—Jeffrey R. Jastrzab
*Attorney, Agent, or Firm*—Schwegman, Lunderberg, Woessner & Kluth P.A.

[57] ABSTRACT

A connector apparatus system and method for providing a direct electrical connection to an implanted medical device for recharging batteries, reprogramming memory, or accessing data. The apparatus consists of a needle-like male connector in conjunction with an implantable female connector that is attached to the implanted medical device and contains a self-resealing elastomeric septum entry port. The female connector comprises a recepticle chamber that is densely packed with a plurality of randomly intertwining, thin, flexible, and conductive metal fibers. External battery charging equipment can be connected to the implanted medical device's internal battery with the connector apparatus system. The required circuit path for recharging can be completed by the use of two single polarity connector pairs, one single polarity connector pair in conjunction with a grounding plate, or one bipolar connector pair. For the bipolar embodiment of the connector, the male portion has two conductors seperated by a sleeve of insulating film while the female portion has two stacked cavities, each with separate sealing septums. A multi-polar embodiment of the connector can be used to interface with the implanted device for functions requiring multiple connections.

24 Claims, 7 Drawing Sheets

APPARATUS FOR MAKING DIRECT ELECTRICAL CONNECTION WITH AN IMPLANTABLE MEDICAL DEVICE

BACKGROUND OF THE INVENTION

1. Field of the Invention

The present invention relates to implantable medical devices. More specifically, the present invention relates to battery-powered implantable devices that receive energy for recharging the battery from an external source. Still more particularly, the invention relates to systems for transmitting energy from an external source to an implanted medical device and for transmitting data between an implanted device and external apparatus.

2. Description of the Relevant Art

Implantable medical devices, such as pacemakers and defibrillators, typically are powered by a battery that is incorporated within the device. Non-rechargeable batteries are commonly used to power the implanted devices. Non-rechargeable batteries, however, have a limited life and thus surgery, including its associated risks, discomfort and cost, is necessary to replace an implanted device once its battery is drained. Because of limited life and other undesirable consequences of using non-rechargeable batteries, the use of rechargeable batteries is desirable. Whereas operational life of an implanted device incorporating a non-rechargeable battery was limited to the duration of the original battery charge, an implanted device using a rechargeable battery can function for significantly longer periods given that the batteries can be recharged repeatedly.

One technique for recharging an implanted devices battery involves transcutaneous energy transmission, a technique which allows non-invasive battery charging. Using transcutaneous energy transmission, such as described in U.S. Pat. No. 5,411,537, an alternating current (AC) in an external primary coil of wire creates a magnetic field which, in turn, induces an AC electrical current in a secondary coil of wire that is housed within the implanted medical device. Charging energy is thus transmitted in the same manner as between the primary and secondary coils of a transformer. The alternating current induced in the implanted secondary coil is then rectified and regulated to provide direct current (DC) power for charging the medical device's battery.

Transcutaneous energy transmission, although generally safe and reliable, is not without certain shortcomings. For example, the efficiency of transcutaneously inducing a current in the implanted coil is detrimentally effected if the internal and external coils are not properly aligned or oriented, or if the distance between the external and internal coils is too great. Because there is no direct physical connection between the external charger and the implanted device to provide feedback, ascertaining whether transmission efficiency is maximized or whether the battery has become fully charged is problematic.

Also, as mentioned previously, transcutaneous energy transmission relies upon a magnetic field to induce an AC current in the implanted coil. At the same time, the alternating magnetic flux generated by the AC current may induce eddy currents in the medical device's metal housing and in the metal casings of various components internal to the implantable device. The magnitude of these eddy currents is a function of the frequency and magnitude of the magnetic flux. Eddy currents cause a temperature increase in the metal components in which the current is conducted. If too great, the temperature increase in the implanted device caused by eddy currents can damage the surrounding body tissues. A high charging current, moreover, creates large temperature rises, thereby increasing the risk of harm to surrounding tissues.

Another known recharging technique uses direct electrical connections between an external power source and an implanted receptacle. For example, U.S. Pat. No. 4,941,472 (Moden, et al) describes an implanted electrical access port to provide a receptacle for receiving needle electrodes. The electrical access port in Moden is electrically interconnected to an implanted medical device. L-shaped needle electrodes of Moden are inserted through the patient's skin and body tissue and inserted into opposite ends of the access port. A center conduit in the needle electrode is made of a conducting material and, except for the needle's tip, is surrounded by an insulating material. The Moden needle electrodes mate in the access port with brush-shaped contact assemblies. Because of the shape of the needle electrode in Moden (L-shaped), insertion of the needle electrodes is cumbersome. Further, as best shown in FIGS. 4 and 5 of Moden, the needles must be inserted into the access port completely and with a small angular tolerance. That is, it is easily possible to insert Moden's needle electrodes into the access port at such an angle that the electrode's tip will not mate with the brush-shaped, contact assembly. In this event, the required electrical connection would not be made. Also, Moden contemplates positioning the access port apart from the implanted medical device, thus requiring two surgical sites in order to implant the entire system.

U.S. Pat. No. 5,205,286 (Soukup, et al.) discloses a subcutaneous data port that provides a plurality of conductive ports for receiving needle electrodes. Multiple needle sticks are required with the Soukup device in order to mate the needles with all of the conductive ports, thus potentially increasing discomfort to the patient. Soukup also contemplates implanting the port separately from the implanted therapeutic device such that incisions in at least two locations are required.

Thus, there remains a need in the art for a system that overcomes these and other problems associated with existing systems for providing recharging current to implanted devices. A means for providing direct electrical connection between the external charging device and the implanted device would eliminate alignment concerns, eliminate the potential for tissue damage caused by the eddy currents generated by transcutaneous energy transmission, eliminate the need for inclusion of internal charging circuitry within the implanted device, and would provide a direct connection between the external charger and battery so as to provide feedback information on the status of battery charging. It would be desirable to provide a system for making a direct electrical connection between an external charging device and an implanted device which minimizes the number of surgical sites required. In particular, it would be desirable to construct an implantable medical device (a pacemaker or defibrillator, for example), that itself includes at least one receptacle, for receiving needle electrodes for recharging a battery in the medical device. It would also be desirable to minimize the number of needle electrodes required to make the required electrical connections, yet at the same time allow for multiple conductors to connect to the implantable device. It would be preferable if all the electrical connections could be made by means of a single needle. It would be further advantageous to provide direct electrical connections to an implantable medical device for, not only recharging the batteries in the medical device, but also other electrical functions such as transferring data to and from the medical device. Despite the substantial advantages that would be afforded by such a system, to date no such system has been developed.

SUMMARY OF THE INVENTION

A connector system and method for providing a direct electrical connection to an implanted medical device is disclosed to recharge batteries, reprogram memory, and/or transmit data. The connector apparatus includes a needle-like male connector in conjunction with an implantable female receptacle connector that is attached to the implanted medical device and contains a self-resealing septum entry port. The needle-like male connector electrode pierces through skin and body tissues and inserts through the septum entry port of the female receptacle connector. The female receptacle includes a receptacle chamber that is densely packed with a plurality of randomly intertwining thin, flexible, and conductive metal fibers that allow easy male connector electrode insertion and electrical contact, while also providing a wide tolerance mating target. The self-resealing septum forms a seal around the entry port of the female receptacle through which the needle connector passes. Upon extraction of the needle connector from the receptacle, the septum reseals the hole through which the needle connector was extracted. The receptacle connectors are preferably housed within the implanted medical device but can be implanted at a remote location from the medical device with properly insulated conductors that connect the receptacles and the medical device. Using two needle connectors, one a positive polarity electrode and the other negative polarity, and two proper polarity mating receptacles, a direct electrical completed circuit path to the implanted device can be made which can be used to recharge an internal battery of the implanted medical device.

One or more coaxially disposed conductive elements may be incorporated onto the needle connector, each conductive element is insulated from other conductive elements by a sleeve of insulating film. A needle connector with multiple conductive elements can be used to recharge the medical device's battery, reprogram memory, extract data stored in memory in the medical device and the like. In this embodiment, the female connector is a multi-chambered receptacle including a separate chamber or receptacle for electrical connection to each corresponding conductive element of the needle connector. The multiple receptacles of this embodiment are coaxially aligned in a stacked relationship. Each receptacle is insulated from the others by means of separate self-resealing septums for each receptacle. Upon needle connector insertion, each conductive element in the needle connector makes electrical contact only with the metal fibers in the respective mating receptacle.

A grounding plate may be used in conjunction with one single polarity connector pair to eliminate one of the two needle penetrations required to provide the completed circuit path for battery recharging. The needle connector may provide a positive or negative polarity terminal and the grounding plate, which is placed in contact with or attached to the surface of the patient's skin in proximity to the implanted device, provides the necessary opposite polarity terminal. The metal housing of the implanted medical device, which is required to be internally connected to one of the internal battery terminals (either permanently or through a switched connection), electrically couples via the conductivity of the patient's body tissue to the grounding plate thus completing the required circuit path.

BRIEF DESCRIPTION OF THE DRAWINGS

Other objects and advantages of the invention will become apparent upon reading the following detailed description and upon reference to the accompanying drawings in which.

DETAILED DESCRIPTION OF THE PREFERRED EMBODIMENTS

Figure 1:
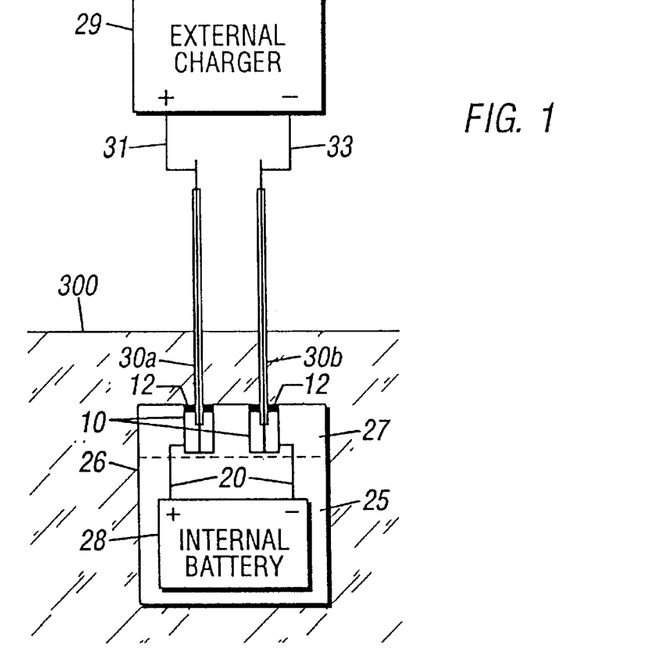
FIG. 1 is a schematic block diagram showing the apparatus and system of the present invention for making a direct electrical connection between an external device and an implanted device using needle electrodes and receptacles to recharge batteries within the implanted device.

Referring now to FIG. 1, a system consistent with a preferred embodiment includes an external charger 29 connected to an implanted medical device 26 through a pair of needle connectors 30a and 30b. Needle connector 30a connects to the positive terminal of external charger 29 via conductor 31 and needle connector 30b connects to the negative terminal of external charger 29 via conductor 33. Implanted device 26, which may be a defibrillator or pacemaker for example, includes housing 25, header 27, receptacles 10, internal battery 28 and conductors 20 for interconnecting receptacles 10 and battery 28. Housing 25 preferably is made of titanium or other biocompatible material and includes an interior chamber for housing battery 28 as well as other conventional circuit components (not shown). Header 27 provides an access area for external connection to implanted medical device's internal circuitry and is made of epoxy for example. Receptacles 10 are preferably embedded in header 27.

As will be explained in greater detail below, receptacles 10 are sealed by self-resealing septums 12. The needle electrodes 30a, 30b pierce the patients skin 300 and are inserted through the underlying tissue and through septums 12 and into receptacles 10 of implanted device 26. Receptacles 10 provide electrical connectivity between the needle electrodes 30a, 30b and conductors 20 which connect to the internal battery 28. In the preferred embodiment thus described, receptacles 10 are housed within the implanted medical device 26, as opposed to being implanted remotely from the device. Housing the receptacles 10 within the implanted device 26 advantageously allows the entire system for making direct electrical connection to be implanted at a single surgical site.

Figure 2A:
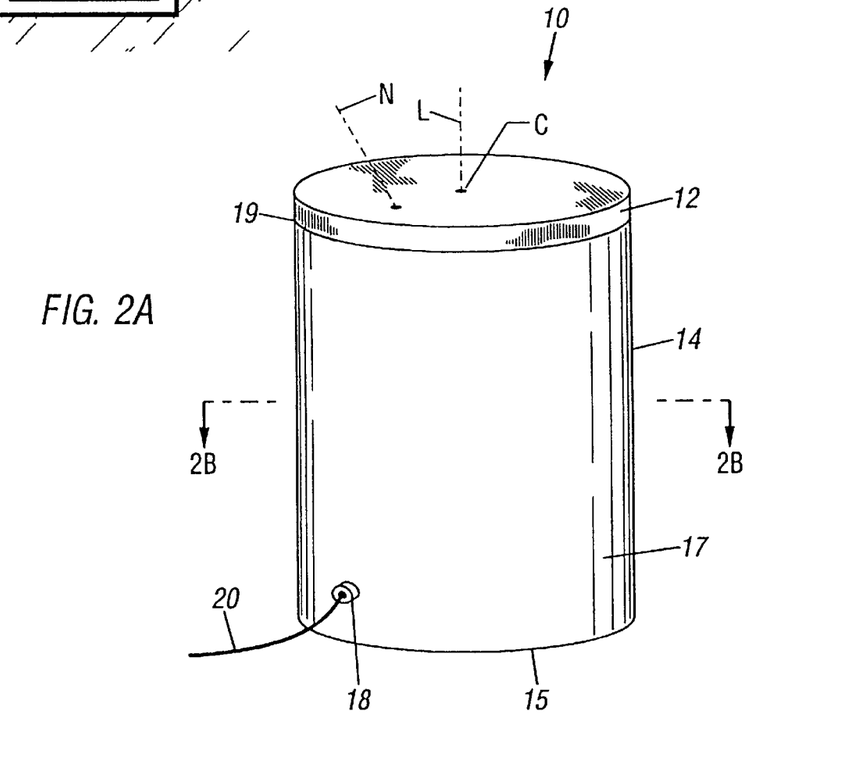
FIG. 2A is a perspective view showing the implantable receptacle of FIG. 1 for receiving a needle electrode.
Figure 2B:
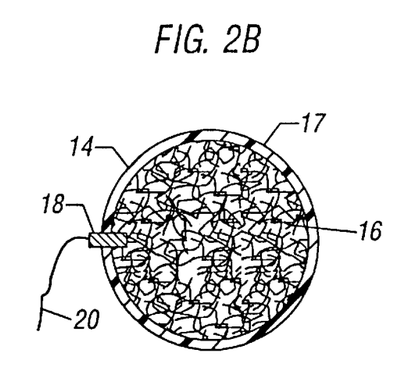
FIG. 2B is a cross-sectional view of the receptacle of FIG. 2A.
Figure 2C:
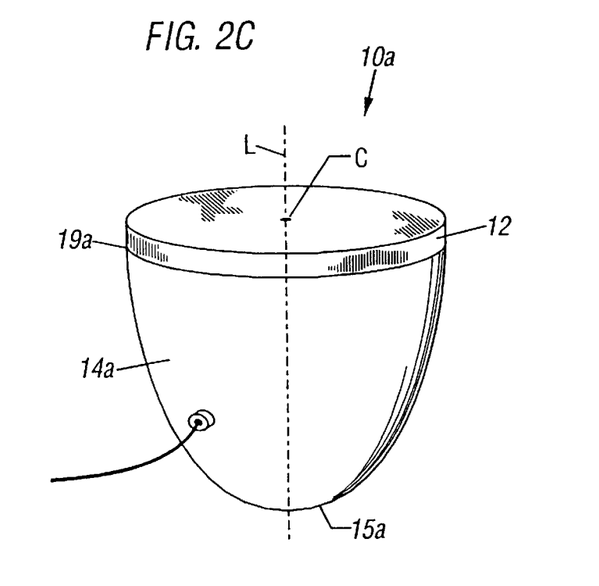
FIG. 2C is a perspective view showing a first alternative embodiment for the implantable receptacle of FIG. 2A.
Figure 2D:
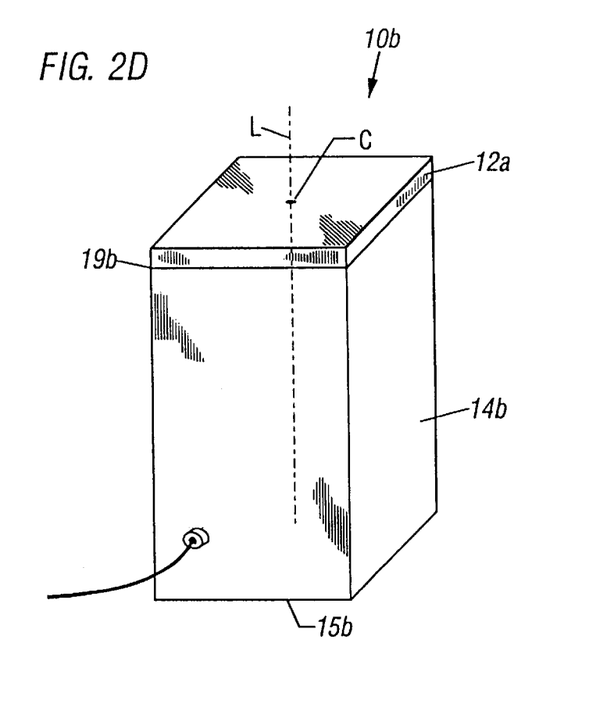
FIG. 2D is a perspective view showing a second alternative embodiment for the implantable receptacle of FIG. 2A.
Figure 3:
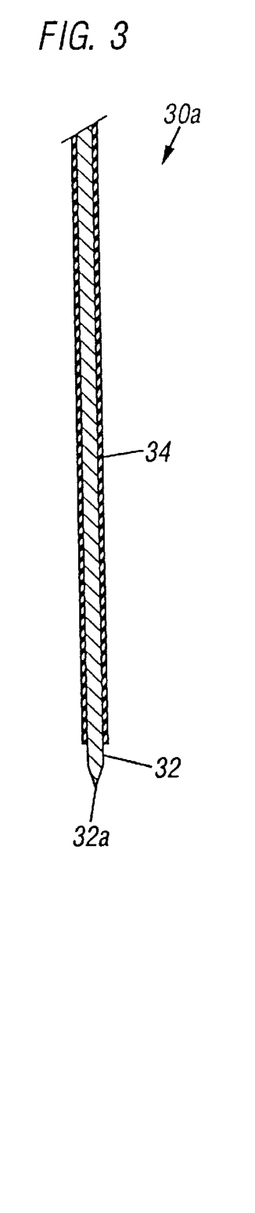
FIG. 3 is an enlarged cross-sectional view of a needle electrode for insertion into the receptacle of FIG. 2A.

Referring now to FIGS. 2A, 2B, and 3, needle electrode 30 and receptacle 10 of the present invention are described in detail. The receptacle 10 includes a self-resealing septum 12 covering a non-conductive receptacle housing 14 which is densely packed with a plurality of randomly intertwining thin, flexible, and conductive metal fibers (analogous to the consistency and texture of a steel wool pad) 16, as best shown in the cross sectional view in FIG. 2B. Receptacle housing 14 is preferably is cylindrical having longitudinal axis L, bottom 15 and sidewall 17 that extends from bottom 15 to upper edge 19. Bottom 15 and sidewall 17 are formed of polyurethane or another biocompatible insulative material. Other shapes and geometries are possible for receptacle 10. For example, there is shown in FIG. 2C a receptacle 10a including a receptacle housing 14a having a generally frustoconical shape and having a circular cross section that tapers from a larger cross sectional area at end 19a to a smaller cross sectional area at the bottom surface 15a. Alternatively, in FIG. 2D a receptacle 10b is shown to include a receptacle housing 14b having a generally rectangular cross section. Receptacle 14b includes a rectangular shaped self-resealing septum 12a at end 19b of receptacle housing 14b. The advantages of these shapes will be addressed in the discussion below.

Referring again to FIGS. 2A and 2B, a conducting member or electrode 18 is attached to and extends through sidewall 17 and contacts the metal fibers 16 or is connected to an inner conductor (not specifically shown) which may be included to ring the inner wall of the cavity to promote conductivity to the fibers. A conducting wire 20 is bonded to conducting member 18, thereby providing an electrical connection between metal fibers 16 and the internal battery 28 of the implanted medical device 26.

Self-resealing septum 12 is made of a nonconducting, biocompatible, elastometric, and self-resealable material such as silicone rubber or polyurethane. The septum 12 provides a closure and seal for receptacle housing 14 to prevent body fluids from entering the receptacle housing 14 or allowing the metal fibers to escape from receptacle housing 14. Septum 12 is attached to the receptacle housing 14 using silicone rubber, polyurethane adhesive or the like. As the needle electrode 30 is inserted through the septum 12, the septum advantageously forms a seal around the electrode substantially preventing body fluids from entering the receptacle housing 14. As the needle is withdrawn from the receptacle 10, the septum 12 automatically reseals the hole from which the needle electrode 30 was extracted.

Referring to FIG. 3, the preferred construction of the needle connectors 30a and 30b is shown with reference to connector 30a, recognizing that connector 30b is substantially the same. Needle connector 30 includes central conducting needle 32 surrounded by an thin insulation layer 34. Central conducting needle 32 is substantially circular in cross section and includes a sharp tip 32a for piercing skin, body tissues, and septum 12. Further, it is preferred that needle electrode 30a be substantially straight. The material from which central conducting needle 32 is made may include "300 series" stainless steel. As shown, only the tip 32a of the needle connector 30a is exposed; the remaining portion of needle connector 30a is covered by a thin layer of insulation 34, preferably polyimide, parylene or other biocompatible, insulating material that has a thickness of approximately 0.1 to 1 mils.

The conductive metal fibers 16 substantially fill the internal volume of the receptacle housing 14. The fibers are preferably made of MP35N alloy, platinum, or other non-corrosive, bio-compatible conducting material. Although the metal fibers 16 include many different shapes and configurations, the fibers are preferably circular in cross section, and approximately 1 mil in diameter. The fibers 16 are packed within receptacle housing 14 with sufficient density to ensure an adequate electrical contact between the fibers and the exposed conducting tip 32a of the needle electrode 30a. At the same time, however, there is sufficient space between fibers to allow needle electrode 30a to be inserted easily through the volume of metal fibers.

As mentioned above regarding the system shown in FIG. 1, the receptacle 10 is implanted within the body as a component of implantable device 26 and receives the needle electrode 30 that is inserted through the skin and body tissues. The needle electrode 30 pierces the septum 12 and is further inserted into the receptacle housing 14. The needle electrode 30 may be inserted through the interior of receptacle housing 14 until the needle tip 32a contacts the bottom 15 of receptacle housing 14. Once the needle electrode 30 makes contact with bottom 15, resistance from further insertion of the needle provides tactile feedback to the doctor or technician indicating that the needle has been fully inserted into the receptacle 10. Other feedback methods could be employed to verify proper insertion and connection to a partially depleted internal battery, such as by using an external voltmeter connected to the connector.

Referring to FIGS. 2A and 3, needle electrode 30a may be inserted at the center C of septum 12. However, the construction of receptacle 10 advantageously allows needle insertion at any other point on septum 12. For example, needle insertion along line N will permit an adequate electrical connection between needle electrode 30a and conducting member 18. The density of metal fibers 16 within receptacle housing 14 ensures electrical conductivity between various adjacent conductive fibers 16 and thus, between the tip 32a of needle electrode 30a and conducting member 18. Consequently, needle electrode 30a may be inserted along a line parallel to longitudinal axis L or at a myriad of other angles less than 90°. Preferably, however, the needle is inserted at an angle between 0° and 30° as measured relative to longitudinal axis L. Moreover, the needle electrode 30a need not be inserted at only one point on septum 12, nor at any one angle. Further, tip 32a need not contact bottom surface 15 for an electrical connection to be made. Tip 32a need only be inserted far enough into the receptacle cavity such that it is not contacting body tissues and is contacting at least one conducting fiber 16 somewhere within receptacle housing 14. Thus, the design of receptacle 10 which permits the insertion of needle electrode 30a at any point on the surface of septum 12 at virtually any angle provides substantial tolerance with respect to making a direct electrical connection during insertion of needle connector 30a.

Alternative embodiments of the invention are shown in FIGS. 4–11. In describing these embodiments, like reference numerals will be used to refer to components or elements that are identical or substantially the same as those previously described.

Figure 4:
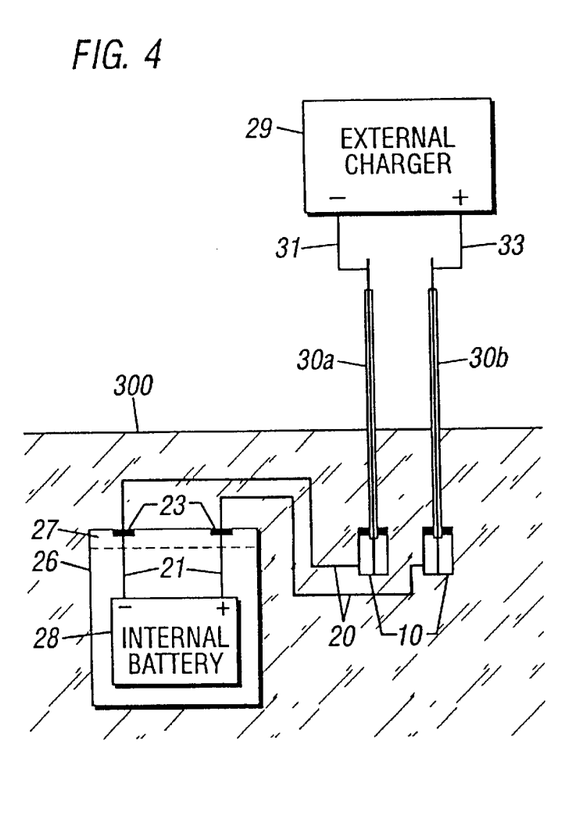
FIG. 4 is a schematic block diagram showing an alternative embodiment of the invention in which the receptacles are implanted separately from the implanted medical device.

Referring now to FIG. 4, receptacles 10 are shown as separate components and are implanted remotely from the implanted medical device 26. Receptacles 10 that have no conductive materials exposed to the patient's body tissues are electrically connected to the implanted medical device 26 by conductors 20 which terminate on terminals 23 in header 27. Terminals 23 are connected to the internal battery 28 via conductors 21. An external charger 29 is connected to the needle electrodes 30a, 30b through conductors 31 and 33. To electrically interconnect external charger 29 to implanted device 26, needle electrodes 30a, 30b are inserted through the skin 300 into receptacles 10. Implanting receptacles 10 remotely from implanted device 26 may be advantageous when, for example, implanted device 26 is deeply implanted or implanted at an angle at which needle insertion would be difficult. It is preferable to avoid sharp edges on the surface of implantable devices exposed to body tissue. Thus, generally round receptacle housing shapes such as those shown in FIGS. 2A and 2C are preferred over the rectangular shape of the housing in FIG. 2D when the receptacles are implanted separate from the implanted device 26.

Figure 5:
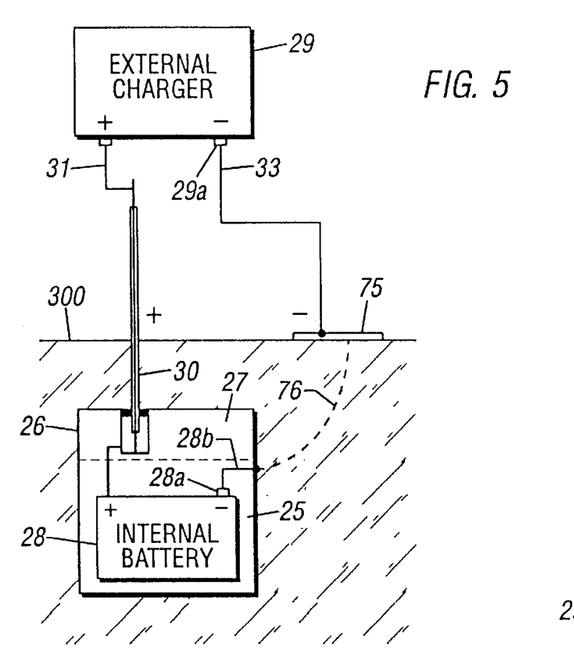
FIG. 5 is a schematic block diagram showing a second alternative embodiment for charging a battery within an implantable medical device using a needle electrode and a grounding plate.

In the embodiments of the invention described with reference to FIGS. 1 and 4, two needles are required, one serving as the positive electrode and a second as the negative electrode. An alternative embodiment is shown in FIG. 5 in which a single needle electrode 30a is used to provide either the positive or negative electrode and a ground plate is used to connect the return terminal. In this instance, the negative terminal 28a of the battery 28 is connected to the metal housing 25 of implanted medical device 26 through conductor 28b. Thus, the external surface of the medical device 26 is at the same electrical potential as the negative terminal of internal battery 28. The negative terminal 29a of the external charger 29 is connected through conductor 33 to a grounding plate 75 which is placed in contact with the skin 300. The negative electrode current path identified as dashed line 76 is completed through body tissue between grounding plate 75 and the metal housing of the implanted medical device 26. This embodiment has the advantage of requiring only one needle penetration to provide a complete electrical circuit path between external charger 29 and implanted device 26 and also allows the use of a less complicated connection system over the bipolar connector system which is described later.

Figure 6:
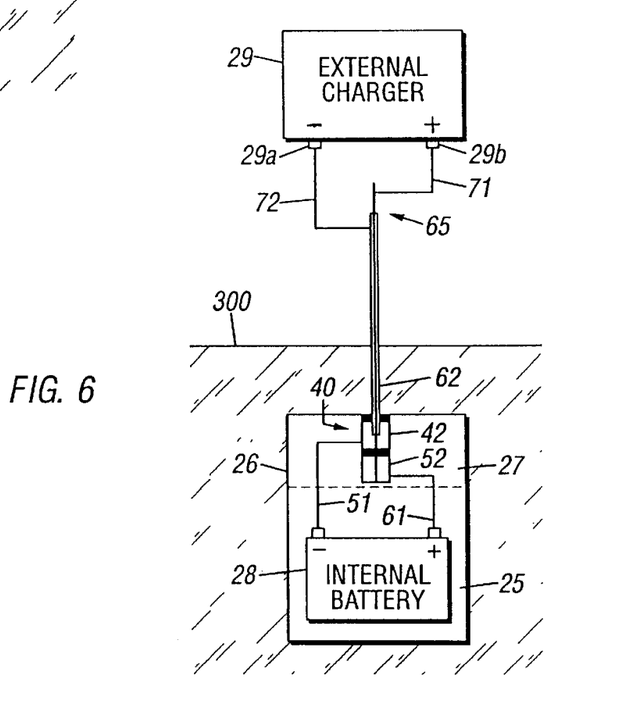
FIG. 6 is a schematic block diagram showing another alternative embodiment of the present invention having a bipolar needle electrode and receptacle to recharge a battery within an implanted medical device.

Referring now to FIG. 6, another alternative embodiment includes a bipolar needle electrode 62 connecting external charger 29 to implanted device 26. Bipolar needle electrode 62 penetrates the skin 300 and mates with dual-chamber receptacle 40 which includes coaxially aligned and stacked receptacles 42, 52. Receptacle 42 connects to the negative terminal of internal battery 28 through conductor 51 and receptacle 52 connects to the positive terminal of the internal battery 28 through conductor 61. Conductor wires 71 and 72 are attached to the conductor electrodes of bipolar connector 62 at the opposite end 65 of the needle connector that pierces and penetrates the skin and implanted receptacles. Conductor 71 connects the bipolar needle connector 62 to the positive terminal 29b of external charger 29, and conductor 72 connects the needle electrode 62 to the negative terminal 29a of external charger 29.

Figure 7:
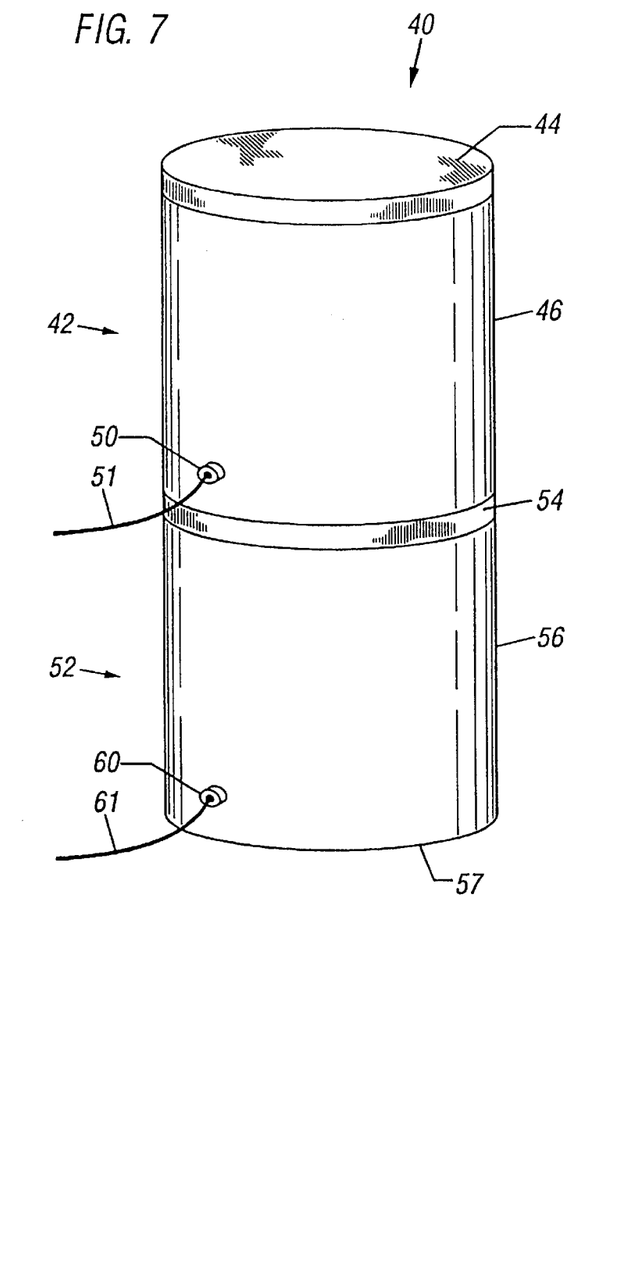
FIG. 7 is a perspective view, similar to FIG. 2A, showing an implantable receptacle for receiving the bipolar needle electrode of FIG. 6.
Figure 8:
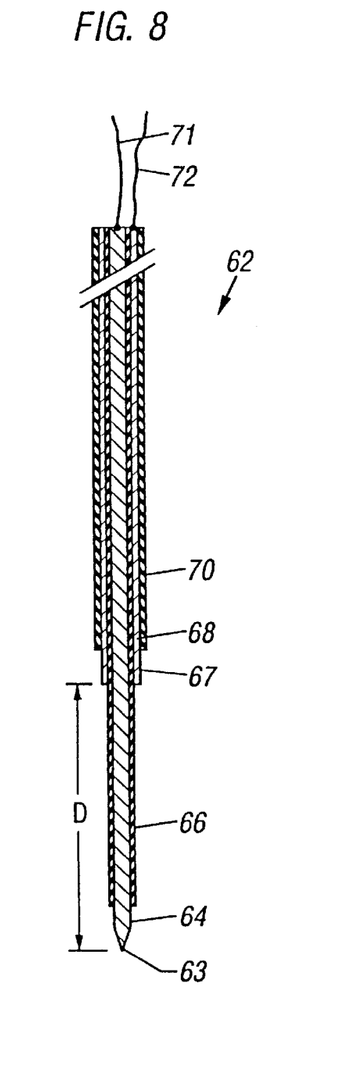
FIG. 8 is an enlarged cross-sectional view of the bipolar needle electrode of FIG. 6.

Referring now to FIGS. 7 and 8, the receptacles 42, 52 and bipolar needle 62 are described in greater detail. The bipolar receptacle connector 40 shown in FIG. 7 includes two receptacles 42, 52 of similar construction to receptacle 10 shown in FIGS. 2A and 2B. Receptacles 42, 52 include septums 44, 54, respectively, which are identical to septum 12 described previously. Receptacle 42 includes a non-conductive receptacle housing 46 sealed at its upper end by septum 44 and is filled with conducting metal fibers 16 previously described. A conductor 51 connects to the metal fibers 16 through a conducting member 50. Conducting member 50 is identical to electrode 18 previously described and is attached to the wall of the receptacle housing 46 and protrudes into the internal volume of the receptacle housing 46 making contact with the metal fibers 16. Receptacle 42 has no bottom and is stacked on top of, and attached or bonded to, receptacle 52. Because receptacle 42 may include no bottom surface, the receptacle housing shapes of FIGS. 2A (cylindrical) and 2D (rectangular) are preferred for stacking than the frustoconical shape of FIG. 2C.

Receptacle 52 includes septum 54 covering a receptacle housing 56 with bottom 57 and is filled with conducting fibers 16. A conductor 61 is coupled to the fibers 16 through a conducting electrode 60 which is identical to electrode 50. With this structure, a needle conductor 62 that is inserted through septum 44 may pass through receptacle housing 46 and through septum 54 and into receptacle housing 56 before making contact with the bottom surface 57 of receptacle housing 56. Septum 54 prevents metal fibers 16 in receptacle 42 from contacting the metal fibers 16 in receptacle 52 and thereby insulates the fibers 16 in receptacle housing 46 from those in receptacle housing 56.

Bipolar needle electrode 62 (FIG. 8) contains a central conducting needle 64 coaxially surrounded by an insulating film 66. Tip 63 of conducting needle 64 is exposed (i.e., not covered by insulating film 66). A conducting film 68 made preferably of platinum covers the upper portion of insulating film 66 beginning a distance D from the tip 63. Film 68 has a thickness of approximately 2 to 10 microns in order to provide a very thin conductive layer to allow ease of needle penetration. A second insulating film 70 surrounds conducting film 68, except for an exposed end portion 67. Insulating film 66, 70 may include materials such as polyimide or parylene. The distance D is selected to be at least as great as the longest length that the needle would be able to penetrate into receptacle 52 when needle connector 62 is inserted at any angle. Selecting D in this manner ensures that the exposed portion 67 does not extend into receptacle 54 even when the tip 63 of needle electrode 62 contacts the bottom surface 57 of receptacle housing 56 at any angle. Thus, when the needle electrode 62 is fully inserted into receptacles 42, 52 (i.e., with tip 63 contacting bottom surface 57), the exposed conducting tip 63 and exposed end portion 67 contact metal fibers 16 in receptacles 42, 52, respectively, thereby completing the desired electrical paths to conductors 61, 51. Insulating film 70 extends up the outer surface of the needle connector 62 with sufficient length to electrically isolate the outer conductor portions of needle connector 62 from body tissue that the needle connector passes through in order to prevent short circuiting. As with the needle receptacle system of FIG. 1, bipolar needle electrode 62 need only be inserted into receptacle 40 to the extent that tip 63 of needle 64 contacts the metal fibers 16 in receptacle 52 and tip 63 is fully inserted into receptacle 52 such that short circuiting to metal fibers 16 in receptacle 42 does not result. When this occurs, exposed portion 67 of conducting film 68 will be in contact with metal fibers 16 in upper receptacle 42. Thus, tip 63 need not contact bottom surface 57; rather tip 63 need only contact at least one of the metal fibers 16 and no metal fibers in receptacle 42 to make the required electrical connection. Likewise, exposed end portion 67 need only contact one metal fiber 16 and not be in contact with any body tissues. Substantial tolerance is thus provided by the present invention for ensuring proper connection between dual receptacle 40 and needle electrode 62.

Referring now to FIGS. 6 and 8, conductor 71 connects to conducting needle 64 and conductor 72 connects to conducting film 68. Bipolar needle electrode 62 thus contains two conductors 64 and 68 arranged coaxially with 68 surrounding 64. Conducting needle 64 can be used as the positive electrode and conducting film 68 can be the negative electrode, or vice versa. Bipolar electrode 62 allows two conductors to be inserted through the skin and to make a direct electrical connection to an implanted medical device using a single needle and requiring only one needle insertion.

The embodiments described above have particular utility when used to connect an external charger to a rechargeable battery that is internal to an implanted medical device. This is typically accomplished by means of two electrical connections (i.e., one positive and one negative terminal). Other functions requiring electrical connection may require connection of more than two conductors.

Figure 9:
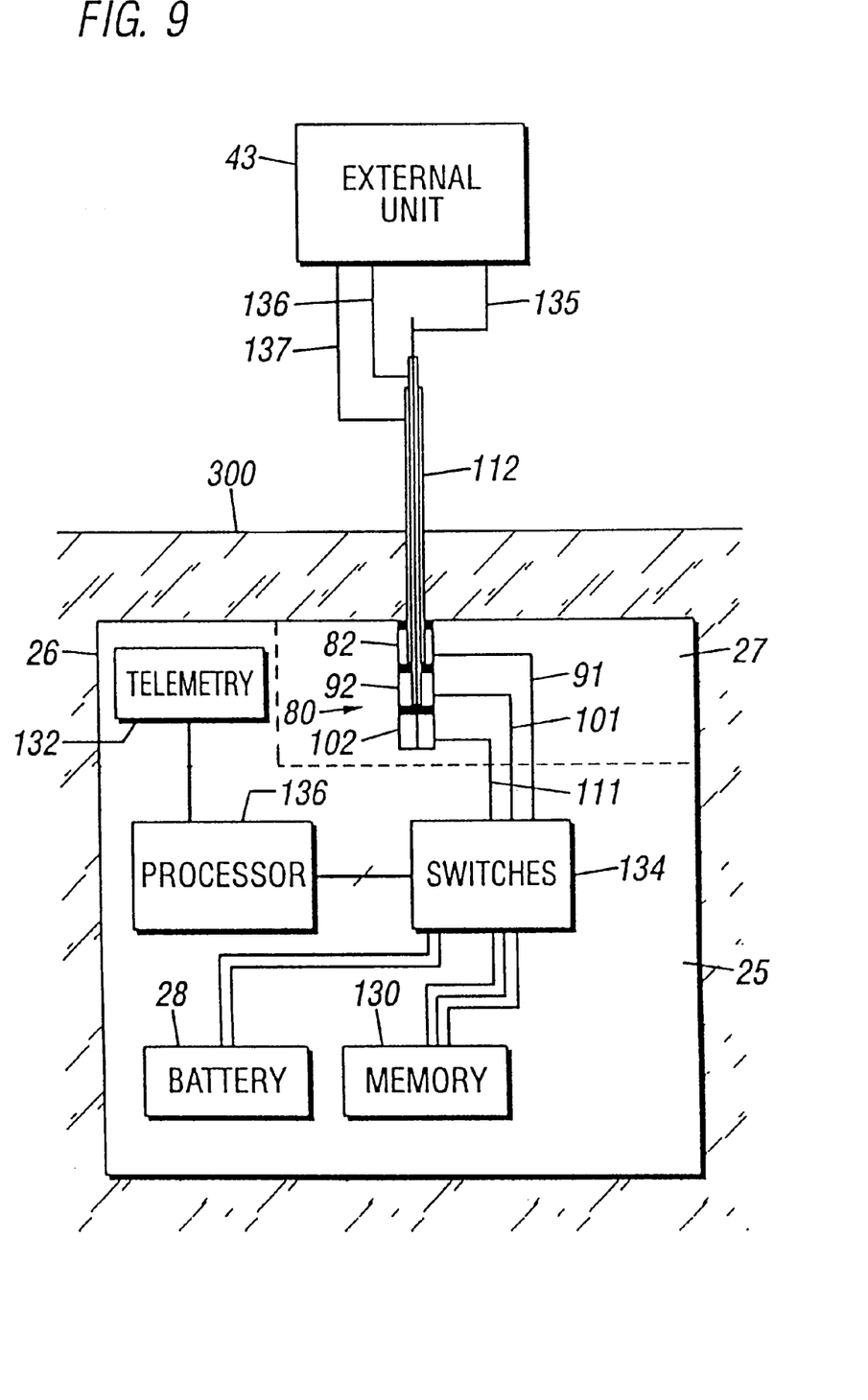
FIG. 9 is a schematic block diagram of another embodiment of the invention having a multi-polar needle electrode for recharging a battery, reprogramming memory or accessing internal data in an implanted medical device.

An embodiment of the present invention providing multiple direct connectors is shown in FIG. 9 and generally includes implantable device 26, external unit 43, and multipolar needle electrode 112 for interconnecting implantable device 26 and external unit 43. As shown in FIG. 9, implantable device 26 includes housing 25 and header 27. Multi-chambered receptacle 80 is disposed in header 27. Housing 25 contains battery 28, microprocessor or control circuitry 136, switches 134, telemetry circuitry 132, and memory 130. Memory 130 may include random access memory (RAM), read only memory (ROM), electrically erasable read only memory (EEPROM), and the like. In general, microprocessor 136 controls operations of the implanted medical device including switches 134 and telemetry 132 which may be used to communicate non-invasively with the microprocessor. Switches 134, interconnected with needle electrode 112 by means of conductors 91, 101, 111, is operable to selectively interconnect battery 28, memory 130 or any other internal circuitry (not shown) to an external unit 43 via multipolar needle conductor 112 and conductors 135, 136 and 137.

The system for making direct electrical connections between external device 43 and implanted medical device 26 shown in FIG. 9 may be employed not only to charge the battery internal to the implantable medical device, but also to provide a direct electrical link with the implantable medical device for purposes such as reprogramming memory or accessing data. It would be desirable, for example, to correct a software code error that has been identified after a device has been implanted or to add a newly developed software feature to an implanted device. Downloading new software to the implanted medical devices reprogrammable memory 130 via switches 134 is accomplished using multi-polar needle electrode 112. EEPROM and RAM integrated circuits are provided in many different configurations requiring different numbers of conductors for reprogramming the devices. Although the needle connector 112 shown in FIG. 9 contains three conductors, one of ordinary skill in the art will recognize that more than three conductors may be necessary or desirable to reprogram a reprogrammable memory circuit of a particular implantable medical device and that more than three conductors can be incorporated into a multi-polar needle electrode 112. The connector could also be used to read data stored in the devices reprogrammable or non-reprogrammable memory.

Telemetry circuitry employed by the implanted device could be used to communicate with the processor 136 to control the state of the switches 134 to route the external connections to their proper internal destinations such as for recharging the battery, reprogramming memory, or reading data.

Figure 10:
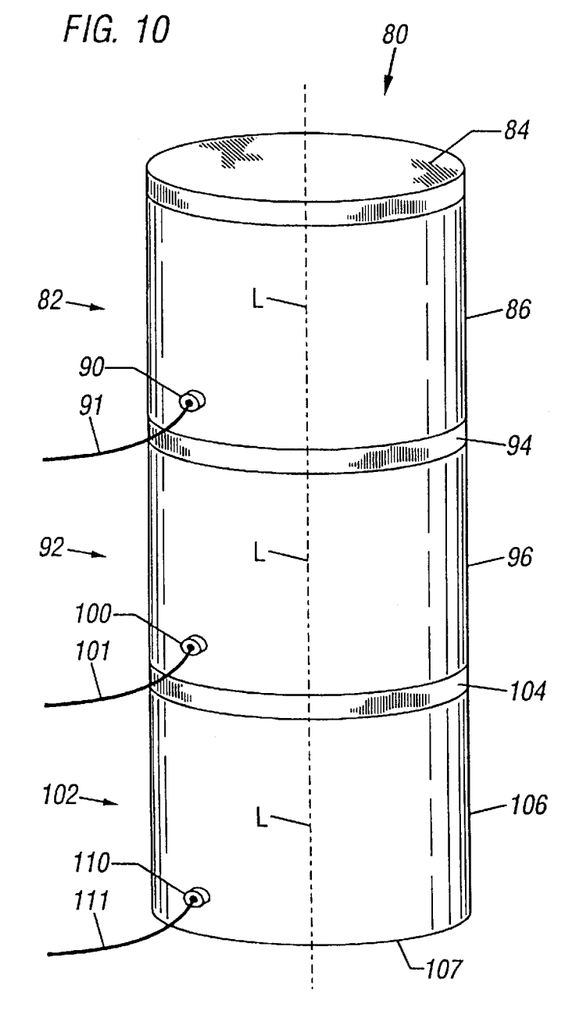
FIG. 10 is an enlarged perspective view of the implantable receptacle of FIG. 9 for receiving a multi-polar needle electrode with three conductors.
Figure 11:
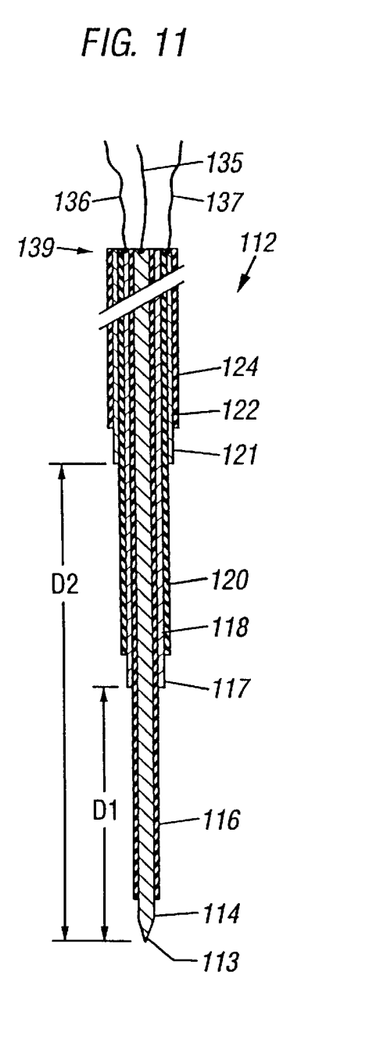
FIG. 11 is an enlarged cross-sectional view showing the multi-polar needle electrode of FIG. 9 including three conductors for mating with the receptacle of FIG. 10.

Referring now to FIGS. 10 and 11, multi-chambered receptacle 80 comprises three receptacles 82, 92 and 102 that are interconnected at their ends and coaxially aligned along axis L. Receptacle 82 includes a bottomless receptacle housing 86 sealed at its upper end by a self-resealing septum 84. Metal fibers 16 substantially fill the internal volume of receptacle housing 86, and a conductor 91 connects to the metal fibers 16 through conducting electrode 90. Similarly receptacle 92 includes a bottomless receptacle housing 96 sealed at its upper end by a self-resealing septum 94 and substantially filled with conducting fibers 16. Septum 94 separates and insulates the metal fibers 16 in receptacle 82 from those of receptacle 92. A conductor 101 connects to the metal fibers 16 in receptacle 92 through conducting electrode 100. Finally, receptacle 102 comprises a receptacle housing 106 having bottom 107. Receptacle housing 106 is sealed at its upper end by a self-resealing septum 104 and is substantially filled with conducting metal fibers 16. A conductor 111 connects to the metal fibers 16 in receptacle 102 through conducting electrode 110. Septum 104 separates and insulates the metal fibers 16 in receptacle 92 from those in receptacle 102. Each septum 84, 94, 104 is preferably identical to septum 12 previously described.

Multi-polar needle electrode 112 adapted for insertion into multi-chambered receptacle 80 is shown to comprise three conducting elements 114, 118, and 122 each conductor separated by an insulators 116, 120, and 124, respectively. Conducting element 114 comprises a central conducting needle identical to the needle connectors of FIGS. 3 and 8. Conducting needle 114 includes an exposed tip 113. Conducting elements 118 and 122 comprise conducting film similar to the conducting film 68 of FIG. 8. Insulating films 116, 120, 124 comprise insulating films of the same construction as the insulating film 66 in needle electrode 62 of FIG. 8. Exposed portions or segments 117, 121 of conducting films 118, 122 provide contact with metal fibers 16 in cans 96, 86, respectively. The lengths of each conductor and insulator are such that with the needle electrode 112 fully inserted and contacting the bottom surface 107 of receptacle 102, the exposed tip 113 of electrode 114 makes contact with metal fibers 16 in receptacle 102, the exposed conducting portion 117 of electrode 118 makes contact with metal fibers 16 in receptacle 92, and the exposed conducting portion 121 of electrode 122 makes contact with the metal fibers 16 of receptacle 82. As shown in FIG. 11, distance D1, which is the distance from the tip 113 to the exposed portion 117 of conducting film 118 ensures that the exposed portion 117 does not enter receptacle 102, but does enter receptacle 92 when the needle electrode 112 is fully inserted with its tip 113 contacting bottom surface 107. Distance D2, which is the distance from the tip 113 to the exposed portion 121 ensures that the exposed portion 121 does not enter receptacle 92, but does enter receptacle 82, when the needle electrode 112 is fully inserted into receptacle 80. Conductors 135, 136, 137 (FIG. 9) are bonded to conducting needle 114, conducting film 118, and conducting film 121, respectively, at the external end 139 of needle electrode 112. Receptacles 82 and 92 have no bottom surface. Therefore, a needle that is inserted into septum 84 of receptacle 82 may pass through the metal fibers 16 in receptacle housing 86, through septum 94, through metal fibers 16 in receptacle housing 96, through septum 104, and into the metal fibers 16 of receptacle housing 106. The needle may then bottom out on the bottom surface 107 of receptacle 102. Thus, the insertion of needle electrode 112 into multi-chambered receptacle 80 permits multiple direct electrical connections between an external unit and an implanted medical device for battery charging or other electrical connection functions with a single needle penetration.

While preferred embodiments of this invention have been shown and described, modifications thereof can be made by one skilled in the art without departing from the spirit or teaching of this invention. The embodiments described herein are exemplary only and are not limiting. Many variations and modifications of the system and apparatus are possible and are within the scope of the invention. Accordingly, the scope of protection is not limited to the embodiments described herein, but is only limited by the claims which follow, the scope of which shall include all equivalents of the subject matter of the claims.

What is claimed is:

1. A system for making a direct electrical connection between an implantable device and an external device comprising:
    a needle connector including a conducting needle electrode having an insulative sleeve disposed about a predetermined length of said needle;
    an implantable receptacle for receiving said needle electrode including a self-resealing septum for covering and sealing said implantable receptacle and including a plurality of conductive fibers substantially filling the implantable receptacle;
    a conductive member attached to a surface of said implantable receptacle and making electrical contact with said plurality of conductive fibers; and
    wherein said needle connector is adapted to be matably engaged with said implantable receptacle to make said direct electrical connection.

2. The system of claim 1 wherein said conductive fibers comprise metal shavings.

3. The system of claim 1, wherein said receptacle is substantially circular in cross section, said cross section being perpendicular to a longitudinal axis passing through said self-resealing septum.

4. The system of claim 3, wherein the area of said cross section is greater at a first end of said receptacle along said longitudinal axis than at a second end of said receptacle along said longitudinal axis.

5. The system of claim 3, wherein said needle electrode is adapted to be matably engaged with said implantable receptacle along a line substantially parallel to said longitudinal axis.

6. The system of claim 3, wherein said needle electrode is adapted to be matably engaged with said implantable receptacle at an angle to said longitudinal axis.

7. The system of claim 6, wherein said angle is between 0° and 30°.

8. The system of claim 1, wherein said receptacle is substantially rectangular in cross section, said cross section being perpendicular to a longitudinal axis passing through said self-resealing septum.

9. The system of claim 1, wherein said implantable receptacle is housed within said implantable device and has a surface for receiving said needle electrode, said surface exposed to the body tissues.

10. The system of claim 9 wherein said implantable device includes a header portion and wherein said receptacle is disposed in said header.

11. The system of claim 1, wherein said implantable receptacle is physically separate from said implantable device and couples to said implantable device through at least one properly insulated conductor.

12. A system for making a direct electrical connection between an implantable medical device and an external device comprising:
    a plurality of aligned receptacles having first and second ends wherein each receptacle includes a non-conductive receptacle housing sealed by a self-resealing septum on a first end of said receptacle housing;
    conductive metal fibers substantially filling each of said receptacle housings and insulated from said conductive fibers in each of said other receptacle housings; and
    a multi-polar needle connector including a plurality of conductors separated by insulating layers and including a center conductor comprising a needle with an exposed tip, said multi-polar needle connector adapted to be matably engaged with said plurality of aligned receptacles.

13. The system of claim 12, wherein the plurality of said receptacles are stacked with said first end of one of said plurality of receptacles mated with said second end of another of said plurality of receptacles.

14. The system of claim 13, wherein said multi-polar needle electrode is adapted to be inserted through the stack of said plurality of receptacles and wherein the exposed tip enters into the receptacle housing of the bottom receptacle of said stack.

15. The system of claim 14, wherein each of said plurality of said conductors in said needle electrode is adapted to make contact with the conductive fibers in only one receptacle housing of said stack.

16. The system of claim 15, wherein the stack of said plurality of said receptacles is housed within said implantable medical device and has a surface for receiving said multi-polar needle electrode, said surface exposed to the body tissues.

17. The system of claim 15, wherein the stack of said plurality of said receptacles is physically separate from said implantable medical device and couples to said implantable medical device through a plurality of conductors.

18. An implantable medical device comprising:
    a receptacle for receiving a needle electrode;
    a rechargeable battery for powering said implantable medical device;
    a reprogrammable memory subsystem for storing software;
    a telemetry circuit for external communication with the implantable medical device;
    a switch for connecting said receptacle to said rechargeable battery and said memory subsystem; and
    a processor controlling the state of said switch.

19. A system for making a direct electrical connection between an implantable device in a patient and an external device comprising:
    a housing for enclosing components of the implantable device;
    a needle connector including a conducting needle having an insulative sleeve disposed about a predetermined length of said conducting needle;
    an implantable receptacle for receiving said needle electrode including a self-resealing septum for covering and sealing said implantable receptacle and including a plurality of conductive fibers substantially filling the implantable receptacle;

a conductive member attached to a side of said implantable receptacle, said conductive member making contact with said plurality of conductive fibers;

a grounding plate in contact with surface of the patient's skin; and wherein said needle electrode is adapted to be matably engaged with said implantable receptacle to make said direct electrical connection.

20. The system of claim 19, wherein said grounding plate provides a positive electrode and said needle connector provides a negative electrode and wherein a positive terminal of a battery in said implantable device is attached to said housing and a current path includes body tissue between said grounding plate and said housing.

21. The system of claim 19, wherein said grounding plate provides a negative electrode and said needle connector provides a positive electrode and wherein a negative terminal of a battery in said implantable device is attached to said housing and a current path includes body tissue between said grounding plate and said housing.

22. A method for providing a direct electrical connection to an implantable medical device to recharge a battery within the medical device and download configuration data to the medical device, comprising the steps of:

(a) inserting a needle electrode containing a conductor through the skin and body tissues;

(b) mating the needle electrode with an implanted receptacle;

(c) transmitting an electrical signal through the needle electrode; and (d) transmitting control signals via telemetry to indicate the status of the implanted device.

23. The method of claim 22, wherein transmitting an electrical signal in step (c) includes transmitting charging current to said battery.

24. The method of claim 22, wherein transmitting an electrical signal in step (c) includes transmitting data through said needle electrode.

* * * * *